(12) United States Patent
Anand et al.

(10) Patent No.: US 10,359,323 B2
(45) Date of Patent: Jul. 23, 2019

(54) TEMPERATURE DISTRIBUTION DETERMINING APPARATUS

(71) Applicant: KONINKLIJKE PHILIPS N.V., Eindhoven (NL)

(72) Inventors: Ajay Anand, Fishkill, NY (US); Balasundar Iyyavu Raju, North Andover, MA (US); Shriram Sethuraman, Briarcliff Manor, NY (US); Junbo Li, Shanghai (CN); John Petruzello, Carmel, NY (US)

(73) Assignee: Koninklijke Philips N.V., Eindhoven (NL)

( * ) Notice: Subject to any disclaimer, the term of this patent is extended or adjusted under 35 U.S.C. 154(b) by 742 days.

(21) Appl. No.: 14/895,514

(22) PCT Filed: Jun. 20, 2014

(86) PCT No.: PCT/EP2014/063004
§ 371 (c)(1),
(2) Date: Dec. 3, 2015

(87) PCT Pub. No.: WO2015/000721
PCT Pub. Date: Jan. 8, 2015

(65) Prior Publication Data
US 2016/0131540 A1    May 12, 2016

Related U.S. Application Data

(60) Provisional application No. 61/842,403, filed on Jul. 3, 2013.

(30) Foreign Application Priority Data

Jul. 19, 2013  (EP) .................................... 13177253

(51) Int. Cl.
*G01K 11/22*    (2006.01)
*A61B 8/08*    (2006.01)
(Continued)

(52) U.S. Cl.
CPC ............ *G01K 11/22* (2013.01); *A61B 8/4444* (2013.01); *A61B 8/48* (2013.01); *A61B 8/5223* (2013.01);
(Continued)

(58) Field of Classification Search
CPC ..... G01K 11/22; A61B 8/4444; A61B 8/5223; A61B 18/1477; A61B 8/54; A61B 8/48;
(Continued)

(56) References Cited

U.S. PATENT DOCUMENTS 5,657,760 A    8/1997 Ying et al.
2001/0007940 A1    7/2001 Tu et al.
(Continued)

FOREIGN PATENT DOCUMENTS

EP    2489398 A1    8/2012
WO    2008112005 A1    9/2008
WO    2012142223 A1    10/2012

OTHER PUBLICATIONS

Azhari, H. "Feasibility Study of Ultrasonic Computed Tomography-Guided High-Intensity Focused Ultrasound" Ultrasound in Medicine and Biology, vol. 38, No. 4, pp. 619-625 (2012).
(Continued)

*Primary Examiner* — Sanjay Cattungal

(57) ABSTRACT

The invention relates to a temperature distribution measuring apparatus for measuring a temperature distribution within an object caused by heating the object. A temperature distribution measuring unit (13, 71) measures the temperature distribution in a measurement region within the object, while the object is heated, and a temperature measurement
(Continued)

control unit (22) controls the temperature distribution measuring unit such that the measurement region is modified depending on the measured temperature distribution, in order to measure different temperature distributions in different measurement regions. This allows, for example, modifying the measurement region depending on an actually measured temperature distribution such that in the modified new measurement region the measurement of the temperature of the object can be continued, if the temperature actually measured in the current measurement region is too high for being accurately measured, thereby extending the time period in which a temperature distribution of the object can be measured.

23 Claims, 6 Drawing Sheets

(51) Int. Cl.
| | | |
|---|---|---|
| | *A61B 8/00* | (2006.01) |
| | *A61B 18/14* | (2006.01) |
| | *A61N 7/00* | (2006.01) |
| | *A61N 7/02* | (2006.01) |
| | *A61B 6/12* | (2006.01) |
| | *A61B 6/00* | (2006.01) |
| | *A61B 17/00* | (2006.01) |
| | *A61B 18/00* | (2006.01) |
| | *A61B 90/00* | (2016.01) |

(52) U.S. Cl.
CPC .......... *A61B 8/54* (2013.01); *A61B 18/1477* (2013.01); *A61N 7/00* (2013.01); *A61N 7/02* (2013.01); *A61B 6/12* (2013.01); *A61B 6/487* (2013.01); *A61B 2017/00106* (2013.01); *A61B 2018/00797* (2013.01); *A61B 2018/00821* (2013.01); *A61B 2090/378* (2016.02); *A61N 2007/0052* (2013.01)

(58) Field of Classification Search
CPC .... A61B 2090/378; A61B 2018/00821; A61B 2018/00797; A61B 2017/00106; A61B 6/12; A61B 6/487; A61N 7/02; A61N 7/00; A61N 2007/0052
USPC .................................................. 600/437–469
See application file for complete search history.

(56) References Cited

U.S. PATENT DOCUMENTS

| | | | |
|---|---|---|---|
| 2011/0060221 A1* | 3/2011 | Fan .................. | A61B 5/015 |
| | | | 600/438 |
| 2012/0010479 A1 | 1/2012 | Eusemann et al. | |
| 2012/0165666 A1 | 6/2012 | Megens et al. | |
| 2013/0046178 A1 | 2/2013 | Cho et al. | |
| 2013/0060243 A1 | 3/2013 | Kuhn | |
| 2013/0079765 A1 | 3/2013 | Kim et al. | |
| 2013/0116560 A1* | 5/2013 | Chen .................. | A61B 8/00 |
| | | | 600/438 |
| 2013/0296743 A1* | 11/2013 | Lee .................. | A61B 8/5223 |
| | | | 601/3 |
| 2016/0008633 A1* | 1/2016 | Vortman .............. | A61N 7/02 |
| | | | 601/2 |

OTHER PUBLICATIONS

Pennes, H.H. "Analysis of tissue and arterial blood temperatures in the resting human forearm", Journal of Applied Physiology (1998), 85:5-34.

Anand, A. et al., "Three-dimensional spatial and temporal temperature imaging in gel phantoms using backscattered ultrasound", IEEE Transactions on ultrasonics, Ferroelectrics and Frequency Control, ICCC, US, vol. 54, No. 1, (2007), pp. 23-31.

Yang, C. et al., "Ultrasound monitoring of temperature and coagulation change during tumor treatment with microwave ablation", Frontiers of Biology in China, vol. 4, No. 3, (2009), pp. 254-259.

Liu, H.L. et al., "Instantaneous frequency-based ultrasonic temperature estimation during focused ultrasound thermal therapy", Ultrasound Med Biol., Oct. 2009;35(10): 1647-61.

* cited by examiner

TEMPERATURE DISTRIBUTION DETERMINING APPARATUS

CROSS-REFERENCE TO PRIOR APPLICATIONS

This application is the U.S. National Phase application under 35 U.S.C. § 371 of International Application Serial No. PCT/EP2014/063004, filed on Jun. 20, 2014, which claims the benefit of U.S. Application Ser. No. 61/842,403, filed on Jul. 3, 2013 and European Patent Application 13177253.5 filed on Jul. 19, 2013. These applications are hereby incorporated by reference herein.

FIELD OF THE INVENTION

The invention relates to a temperature distribution determining apparatus, a temperature distribution determining method and a computer program for determining a temperature distribution within an object caused by heating the object. The invention relates further to a system for heating the object comprising the temperature distribution determining apparatus.

BACKGROUND OF THE INVENTION

The article "Feasibility Study of Ultrasonic Computed Tomography-Guided High-Intensity Focused Ultrasound" by H. Azhari et al., Ultrasound in Medicine and Biology, volume 38, number 4, pages 619 to 625 (2012) discloses a temperature distribution measuring apparatus for measuring a temperature distribution within tissue during a high-intensity focused ultrasound (HIFU) breast treatment procedure. The apparatus comprises an ultrasound imaging device for generating images depicting the speed of sound within the tissue, wherein based on changes in the speed of sound temperature elevations, which occur during the HIFU breast treatment procedure, are determined.

The article "Ultrasound monitoring of temperature and coagulation change during tumor treatment with microwave ablation" by C. Yang et al., Frontiers of Biology in China, volume 4, number 3, pages 254 to 259 (2009) discloses several methods for estimating a temperature distribution within tissue during a microwave ablation therapy procedure by using correlations between ultrasound characteristics of the tissue and the temperature of the tissue.

The article "Three-dimensional spatial and temporal temperature imaging in gel phantoms using backscattered ultrasound" by A. Anand et al., IEEE Transactions on Ultrasonics, Ferroelectrics and Frequency Control, 54(1), pages 23 to 31 (2007) discloses an ultrasound thermometry system being adapted to determine the temperature of an object based on ultrasound signals backscattered by the object. In particular, the system is adapted to determine the speed of sound within the object from the backscattered ultrasound signals and to determine the temperature of the object based on the determined speed of sound.

This kind of determining the temperature of the object requires that the relationship between the speed of sound and the temperature of the object is linear, i.e. the temperature range in which the temperature of the object is measurable by the system is delimited by the temperature range in which the relationship between the speed of sound and the temperature is linear. If the object is heated, the temperature of the object can only be measured, as long as the temperature of the object is within this temperature range, thereby limiting the time period during which the temperature of the object can be measured while heating the object.

SUMMARY OF THE INVENTION

It is an object of the present invention to provide a temperature distribution determining apparatus, a temperature distribution determining method and a computer program for determining a temperature distribution within an object caused by heating the object, which allows determining the temperature distribution within the object over a longer time. It is a further object of the present invention to provide a system for heating the object, which comprises the temperature distribution determining apparatus.

In a first aspect of the present invention a temperature distribution measuring apparatus for measuring a temperature distribution within an object caused by heating the object is presented, wherein the temperature distribution measuring apparatus comprises:

a temperature distribution measuring unit for measuring the temperature distribution in a measurement region within the object, while the object is heated, wherein the temperature distribution measuring unit comprises an ultrasound probe for acquiring ultrasound data of the measurement region and an ultrasound thermometry unit for determining the temperature distribution within the measurement region based on the acquired ultrasound data, a temperature measurement control unit for controlling the temperature distribution measuring unit such that the measurement region is modified depending on the measured temperature distribution, in order to measure different temperature distributions in different measurement regions, a model providing unit for providing a model of the object describing a model temperature distribution
  a) in the measurement regions for time periods, in which the respective temperature distribution has been measured in the respective measurement region, and
  b) in the measurement regions for time periods, in which the respective temperature distribution has not been measured in the respective measurement region, and/or in a non-measurement region within the object, in which a temperature distribution is not measured, and a temperature distribution estimation unit for determining estimated temperature distributions in the different measurement regions for time periods, in which the respective temperature distribution has not been measured in the respective measurement region and/or in the non-measurement region based on the measured temperature distributions by using the provided model.

Since the temperature measurement control unit controls the temperature distribution measuring unit such that the measurement region is modified depending on the measured temperature distribution, in order to measure different temperature distributions in different measurement regions, the measurement region can be adapted to the currently measured temperature distribution. This allows, for example, modifying the measurement region depending on an actually measured temperature distribution such that in the modified measurement region, i.e. in the new measurement region, the measurement of the temperature of the object can be continued, if the temperature actually measured in the current measurement region is too high for being accurately measured, thereby extending the time period in which a temperature distribution of the object can be measured.

The temperature distribution is preferentially a temporally and optionally also a spatially dependent distribution. The temperature distribution measuring unit is preferentially adapted such that the measurement region is formed by a plane. The measurement region can be formed by one or several planes, which may be vertical and/or horizontal. However, the measurement region may also be non-planar, in particular, curved.

In an embodiment the temperature measurement control unit is adapted to control the temperature distribution measuring unit such that the measurement region is modified by changing the position of the measurement region. In particular, if the object is heated by a heating source, the temperature measurement control unit may be adapted to control the temperature distribution measuring unit such that the measurement region is consecutively located at different positions, wherein, if the position of the measurement region is changed, it is changed from a position being closer to the heating source to a position being more distant to the heating source. By providing different measurement regions having different distances to the heating source the measurement of a temperature distribution can be continued in another measurement region being more distant to the heating source than the current measurement region, when the temperature distribution measuring unit is not able any more to measure the temperature in the current measurement region. Thus, by increasing the distance of the respective measurement region to the heating source during the heating process the time period, during which the temperature of the object can be measured, can be increased very effectively in a relatively simple way.

The object is preferentially a living being like a person or an animal and the heating source is preferentially an energy application element like a needle or a catheter being adapted to apply energy. The energy is preferentially radio frequency (RF) energy such that the catheter or needle preferentially comprises a corresponding RF electrode. The heating source is preferentially adapted to perform an ablation procedure for ablating, for instance, a tumor.

The ultrasound probe may comprise a one-dimensional or two-dimensional ultrasound transducer for acquiring the ultrasound data, i.e. for scanning the measurement region. This allows measuring the temperature distribution in the measurement regions during the heating process in a technically not very complex way, in particular in comparison with known magnetic resonance based temperature distribution measuring devices.

The temperature distribution measuring device may be adapted to move the ultrasound probe for changing the position of the measurement region, in order to modify the measurement region. In this case the ultrasound probe is preferentially a one-dimensional ultrasound probe. This allows using a technically relatively simple ultrasound probe for measuring the temperature distribution in different measurement regions, which have different distances to the heating source. The ultrasound probe may also be adapted such that the position of the measurement region is changeable without moving the ultrasound probe. In this case the ultrasound probe is preferentially a two-dimensional ultrasound probe. This allows providing the ultrasound probe without requiring a mechanical movement apparatus for moving the ultrasound probe relative to the heating source, which can lead to a mechanically simpler temperature distribution measuring unit.

It is further preferred that the temperature distribution measuring unit and the temperature measurement control unit are adapted such that the ultrasound probe acquires reference ultrasound data for the different measurement regions at reference temperatures and actual ultrasound data for the different measurement regions and that the ultrasound thermometry unit determines a temperature distribution in a respective measurement region depending on respective actual ultrasound data acquired for the respective measurement region, the reference ultrasound data acquired for the respective measurement region and the respective reference temperature. In particular, the temperature distribution measuring unit and the temperature measurement control unit are adapted such that in a reference data acquisition stage the ultrasound probe acquires the reference ultrasound data for the different measurement regions at known reference temperatures and that in a temperature distribution measurement stage the ultrasound probe acquires actual ultrasound data and the ultrasound thermometry unit determines the temperature distributions in the different measurement regions depending on respective actual ultrasound data acquired for the respective measurement region, the reference ultrasound data acquired for the respective measurement region and the respective reference temperature. The reference temperature can be the same for each measurement region. For instance, if the object is a person, the reference temperature may be 37 degrees Celsius. In particular, if the heating source is an ablation element for ablating a part of the person like a tumor, before the ablation procedure is started, in the reference data acquisition stage the ultrasound probe can acquire the reference ultrasound data, wherein in this case the person has a known temperature of about 37 degrees Celsius. Then, during the ablation procedure the temperature distributions can be measured in the different measurement regions, without requiring an acquisition of reference data during the ablation procedure, thereby fastly and accurately measuring the temperature distributions during the ablation procedure by ultrasound thermometry.

In another preferred embodiment the model providing unit is adapted to provide the model such that it describes a model temperature distribution in the measurement regions, in which the respective temperature distribution has been measured already, and in the measurement regions, in which the respective temperature distribution has not been measured already, depending on modifiable model parameters, wherein the temperature distribution estimation unit is adapted to determine the reference temperature for a respective measurement region, in which the respective temperature distribution has not been measured already, by modifying the model parameters such that a deviation of the model temperature distribution in the measurement regions, in which the respective temperature distribution has been measured already, from the measured temperature distributions in the measurement regions, in which the respective temperature distribution has been measured already, is minimized and by determining the reference temperature from the modified model. Thus, in this embodiment the temperature distributions can be measured in the different measurement regions, without requiring an acquisition of reference ultrasound data at known reference temperatures in a previous reference data acquisition stage.

The temperature measurement control unit is preferentially adapted to determine whether the measured temperature distribution in the measurement region includes a temperature outside a predefined temperature range and to control the temperature distribution measuring unit such that the measurement region is modified, if the measured temperature distribution in the measurement region includes a temperature outside the predefined temperature range. In an embodiment the object is a person or an animal and the predefined temperature range is defined by an upper maximum temperature of 50 degrees Celsius. The predefined temperature range may be further defined by a lower minimum temperature being equal to the normal temperature of the person or animal, in particular, being 37 degrees Celsius.

It is preferred that a) the model providing unit is adapted to provide the model of the object such that it describes the model temperature distribution depending on modifiable model parameters, and b) the temperature distribution estimation unit is adapted to determine the estimated temperature distributions in the different measurement regions for time periods, in which the respective temperature distribution has not been measured in the respective measurement region, and/or in the non-measurement region by modifying the model parameters such that a deviation of the model temperature distribution in the different measurement regions for the time periods, in which the respective temperature distribution has been measured in the respective measurement region, from the measured temperature distributions in the different measurement regions is minimized and by determining the estimated temperature distributions from the modified model. Preferentially, the temperature distribution estimation unit is adapted to estimate the temperature distributions, while the object is heated.

The model parameters are modified during the application of energy, wherein preferentially the temperature dependence of the model parameters within a temperature range, in which the temperature distribution measuring unit cannot measure a temperature distribution, is considered, while determining estimated temperature distributions for these high temperatures, by considering the model temperature distribution, thereby improving the accuracy of determining the estimated temperature distributions in the measurement regions for time periods, in which the temperature in the respective measurement region cannot be directly measured by the temperature distribution measuring unit. For instance, if the temperature distribution measuring unit can measure the temperature distributions only in a temperature range including temperatures below 50 degrees Celsius, the temperature dependence of the model parameters in a temperature range including temperatures higher than 50 degrees Celsius can be considered, while estimating temperature distributions in measurement regions for time periods, in which the temperature in these measurement regions is larger than 50 degrees Celsius, in order to improve the accuracy of determining the estimated temperature distributions in these measurement regions for these time periods.

The modifiable parameters include preferentially thermal parameters like the thermal conductivity and/or electrical parameters like the electrical conductivity of the object. If the object is spatially inhomogeneous, also the modifiable parameters are preferentially spatially inhomogeneous, wherein the spatial inhomogeneity of the modifiable parameters corresponds to the spatial inhomogeneity of the object. For instance, the object can be a part of a living being comprising different elements like different kinds of tissue, blood vessels, et cetera, wherein for at least some of these different elements of the part of the living being different modifiable parameters can be provided by the model.

It is also preferred that the model providing unit is adapted to initialize the provided model with initial model parameters, wherein at least one initial model parameter is an object-specific model parameter. For instance, if the object is a living being comprising blood vessels, the flow velocity within the blood vessels can be determined by, for instance, an ultrasound Doppler technique, wherein the flow velocity can be an initial model parameter, which is object-specific and which can be modified by the temperature distribution estimating unit for adapting the model to the first temperature distribution in the first region and optionally also to a temperature measured at the energy application element. Using initial object-specific model parameters can further improve the accuracy of estimating the second temperature distribution in the second temperature range.

In another aspect of the present invention a system for heating an object is presented, wherein the system comprises a heating source for heating the object and a temperature distribution determining apparatus for determining a temperature distribution within the object as defined in claim 1. The system may further comprise a heating source control unit for controlling the heating source depending on the determined temperature distribution.

In a further aspect of the present invention a temperature distribution measuring method for measuring a temperature distribution within an object caused by heating the object is presented, wherein the temperature distribution measuring method comprises:

measuring the temperature distribution in a measurement region within the object, while the object is heated, by a temperature distribution measuring unit, wherein the temperature distribution measuring unit comprises an ultrasound probe which acquires ultrasound data of the measurement region and an ultrasound thermometry unit which determines the temperature distribution within the measurement region based on the acquired ultrasound data, and controlling the temperature distribution measuring unit such that the measurement region is modified depending on the measured temperature distribution, in order to measure different temperature distributions in different measurement regions, by a temperature measurement control unit, providing a model of the object describing a model temperature distribution a) in the measurement regions for time periods, in which the respective temperature distribution has been measured in the respective measurement region, and b) in the measurement regions for time periods, in which the respective temperature distribution has not been measured in the respective measurement region, and/or in a non-measurement region within the object, in which a temperature distribution is not measured, by a model providing unit, and determining estimated temperature distributions in the different measurement regions for time periods, in which the respective temperature distribution has not been measured in the respective measurement region and/or in the non-measurement region based on the measured temperature distributions by using the provided model by a temperature distribution estimation unit.

In another aspect of the present invention a computer program for determining a temperature distribution within an object caused by heating the object is presented, wherein the computer program comprises program code means for causing a temperature distribution determining apparatus as defined in claim 1 to carry out the steps of the temperature distribution determining method as defined in claim 13, when the computer program is run on a computer controlling the temperature distribution determining apparatus.

It shall be understood that the temperature distribution measuring apparatus of claim 1, the system of claim 11, the temperature distribution measuring method of claim 13, and the computer program of claim 14 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
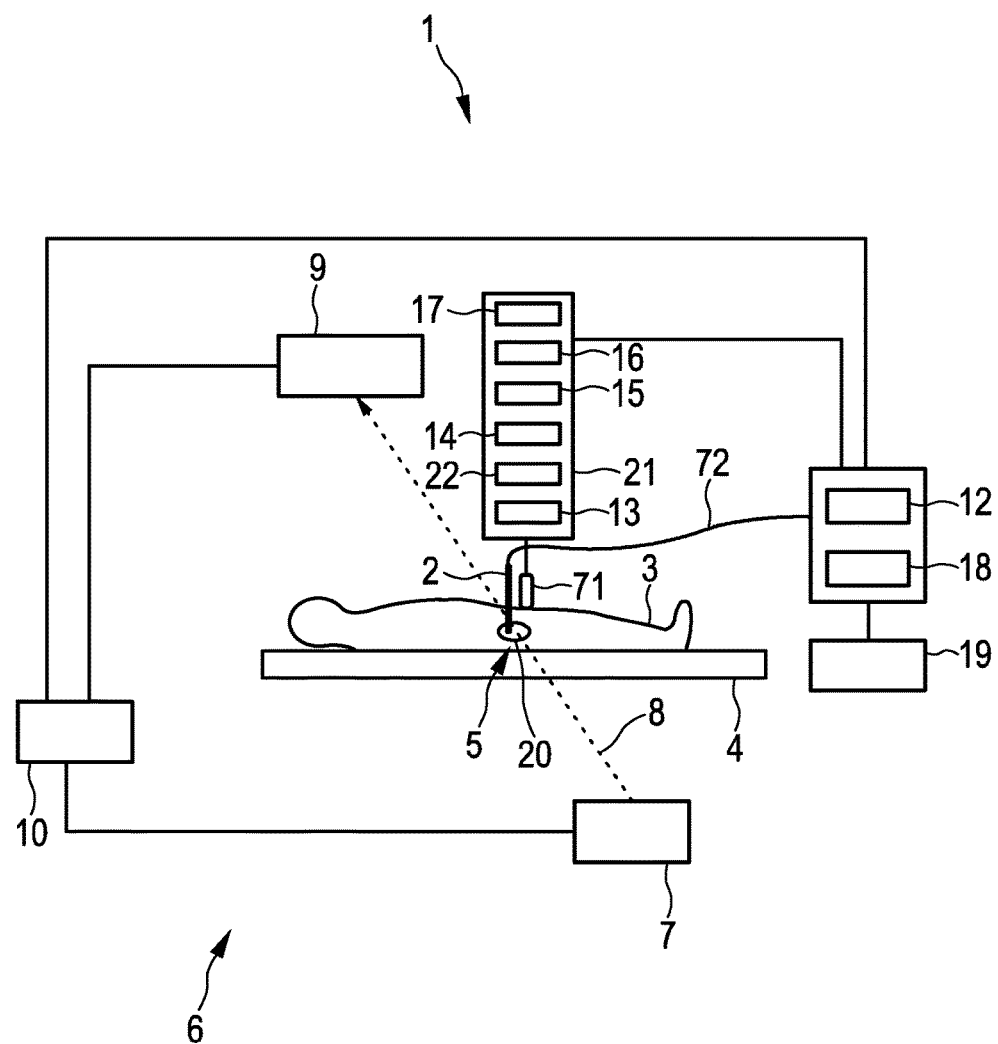
FIG. 1 shows schematically and exemplarily an embodiment of a system for heating an object.

FIG. 1 shows schematically and exemplarily an embodiment of a system for heating an object. In this embodiment the system is an ablation system for ablating a tumor within a person 3 lying on a support means 4 like a patient table. The system 1 comprises an energy application element, i.e. a heating source, for applying energy to a person 3, in particular, to a tumor within a liver 20 of the person 3. The energy application element 2 is an ablation needle comprising ablation electrodes and temperature sensing elements at the tip 5 of the ablation needle 2. The temperature sensing elements at the tip 5 of the ablation needle 2 are preferentially thermocouples, which are electrically connected to a tip temperature measurement determining unit 18 for determining the temperature at the tip 5 of the ablation needle 2 depending on electrical signals received from the thermocouples. The energy applied to the person 3 by the ablation electrodes is preferentially RF energy, wherein the ablation electrodes are electrically connected to an ablation energy control unit 12, i.e. a heating source control unit, for controlling the application of the RF energy via an electrical connection 72. In this embodiment the ablation energy control unit 12 comprises an RF source for providing the RF energy.

Figure 2:
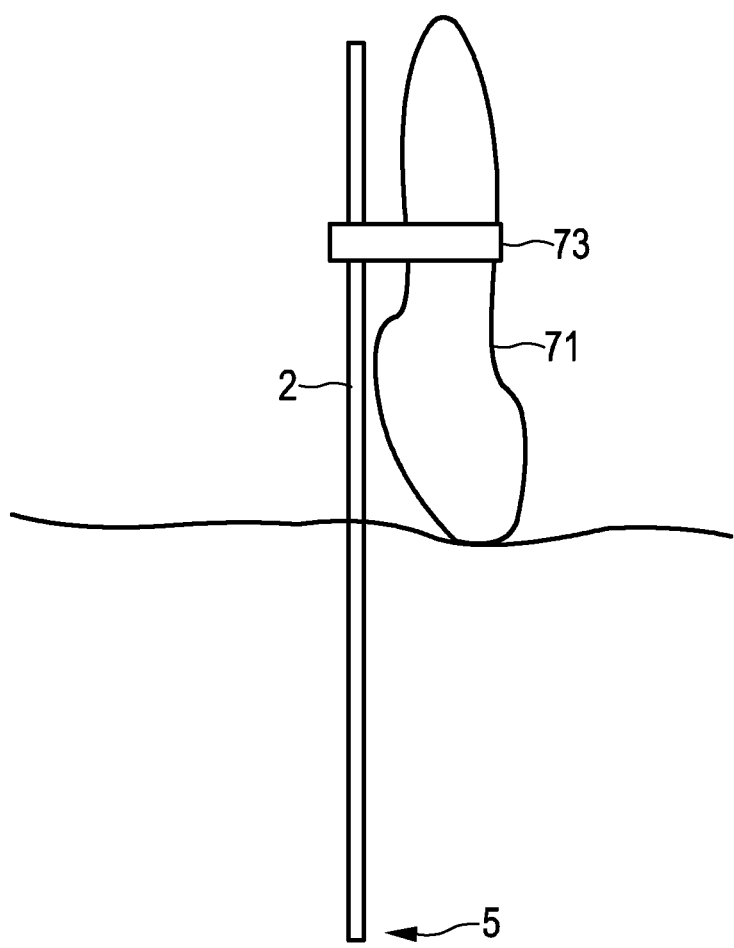
FIG. 2 shows schematically and exemplarily an arrangement of an ultrasound probe, an ablation needle and a fixture, FIG. 3 schematically and exemplarily illustrates several measurement regions having different distances to an ablation needle.

The system 1 further comprises a temperature distribution measuring unit for measuring a spatially and temporally dependent temperature distribution in a measurement region within the person 3, while the RF energy is applied to the person 3. The temperature distribution measuring unit comprises an ultrasound probe 71, which may be fixed to the ablation needle 2, for acquiring ultrasound data of the measurement region and an ultrasound thermometry unit 13 for determining the temperature distribution based on the acquired ultrasound data such that the temperature distribution in the measurement region is measurable by ultrasound thermometry. An arrangement of the ablation needle 2, the ultrasound probe 71 and the fixture 73 is schematically and exemplarily shown in FIG. 2.

The system 1 further comprises a temperature measurement control unit 22 for controlling the temperature distribution measuring unit, in particular, the ultrasound probe 71, such that the measurement region is modified depending on the measured temperature distribution, in order to measure different temperature distributions in different measurement regions. In this embodiment the temperature measurement control unit 22 is adapted to control the temperature distribution measuring unit such that the measurement region is modified by changing the position of the measurement region. In particular, in this embodiment the measurement region is formed by a plane, wherein the temperature measurement control unit 22 is adapted to control the temperature distribution measuring unit such that the planar measurement region is consecutively located at different positions, wherein, if the position of the measurement region is changed, it is changed from a position being closer to the ablation needle 2 to a position being more distant to the ablation needle 2.

The temperature measurement control unit 22 can comprise a storing unit, in which a sequence of predefined positions is stored, wherein during the actual measurement this stored predefined sequence can be used for positioning the planar measurement region. The different positions can be equidistant such that it is just required to store a single distance value and a direction for defining the sequence of positions. However, the sequence of positions can also comprise non-equidistant positions such that the positions may be stored by storing a sequence of distance values, which are at least partly different, and a direction. The sequence of positions can be predefined based on calibration measurements or it can be manually predefined by a user as desired. The sequence of positions can also be predetermined by thermal modeling using a database of typical tissue electrical and thermal properties and organ-specific characteristics. Based on the thermal model the positions with relatively high thermal gradients can be identified and these positions can be avoided, wherein also positions with relatively low thermal gradients can be identified and used for defining the positions of the scan planes. Thus, based on the thermal model thermal gradients can be determined and the sequence of positions may be determined by thresholding the thermal gradients. The thermal gradients used for predetermining the sequence of positions are preferentially spatial gradients.

In an embodiment the predetermination of the sequence of positions may also include the expected temperature rise at the respective position, wherein a position at which the temperature will expectedly rise up to 50 degrees Celsius is preferred in comparison to a position at which the temperature will expectedly not rise to such a high temperature during the modeled heating process. For instance, for each position a selection factor may be calculated being a combination, in particular, a linear combination, of a first value being indicative of the expected temperature rise at the respective position and a second value being indicative of the expected temperature gradient at this position during the modeled heating process, wherein the sequence of positions can be predetermined based on the calculated selection factors. Preferentially, the first value increases with an increasing expected temperature rise and the second value increases with a decreasing expected temperature gradient. The temperature gradient used for the determination of the positions is preferentially the highest spatial temperature gradient to be expected at the respective position during the modeled heating process. For modeling the heating process known bioheat transfer models can be used as the thermal model, which may be implemented by using multiphysics finite elements tools such as COMSOL. Different positions of the planar measurement regions, i.e. of the different ultrasound scan planes, are schematically and exemplarily illustrated in FIG. 3.

Figure 3:
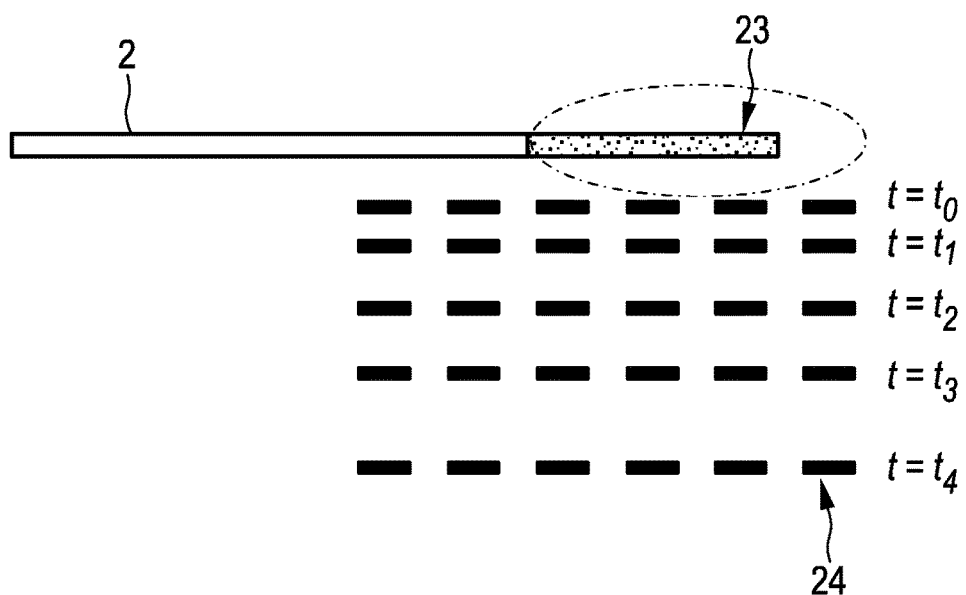

FIG. 3 shows the ablation needle 2 with a heating region 23 formed by ablation electrodes (not shown) located in the heating region 23. The temperature measurement control unit 22 is adapted to control the temperature distribution measuring unit, in particular, the ultrasound probe 71, such that the different measurement regions correspond to different distances of the ultrasound scan plane to the ablation needle 2. The corresponding different measurement regions 24 are indicated in FIG. 3 by broken lines. At an initial time $t_0$ the temperature distribution is measured in a first measurement region being relatively close to the ablation needle 2. When the measured temperature distribution in the current measurement region at the time $t_0$ includes a temperature outside of a predefined temperature range being preferentially a temperature range having a maximum temperature of 50 degrees Celsius, the temperature measurement control unit 22 controls the temperature distribution measuring unit such that the measurement region is modified for measuring the temperature distribution in a second measurement region by changing the position of the measurement region. In FIG. 3 the second measurement region corresponds to the ultrasound scan plane at the time $t_1$. The temperature distribution measuring unit then measures the temperature distribution in this second measurement region and, when the measured temperature distribution includes a temperature being outside of the predefined temperature range, the temperature measurement control unit 22 controls the temperature distribution measuring unit such that the temperature distribution is measured in a third measurement region indicated in FIG. 3 by the ultrasound scan plane at the time $t_2$. This moving from measurement region to measurement region, in particular, from ultrasound scan plane to ultrasound scan plane, is continued with further, more distant measurement regions like the measurement regions indicated in FIG. 3 by the broken lines at the times $t_3$ and $t_4$.

In this embodiment the ultrasound probe 71 comprises a two-dimensional ultrasound transducer for acquiring the ultrasound data of the different measurement regions, i.e. in this embodiment of the different ultrasound scan planes. This allows acquiring the ultrasound data of the different measurement regions without mechanically moving the ultrasound probe 71. In another embodiment the ultrasound probe can comprise a one-dimensional ultrasound transducer, wherein in this case the one-dimensional ultrasound transducer is mechanically movable with respect to the ablation needle 2, in order to acquire ultrasound data of the different measurement regions having the different distances to the ablation needle.

The temperature distribution measuring unit 13, 71 and the temperature measurement control unit 22 are adapted such that the ultrasound probe 71 acquires reference ultrasound data of the different measurement regions 24 at reference temperatures and actual ultrasound data of the different measurement regions 24 and that the ultrasound thermometry unit 13 determines the temperature distribution in the respective measurement region 24, i.e. in the ultrasound scan plane having the respective distance to the ablation needle 2, depending on respective actual ultrasound data acquired for the respective measurement region 24, the reference ultrasound data acquired for the respective measurement region 24 and the respective reference temperature. In particular, the ultrasound thermometry unit 13 is preferentially adapted to determine a three-dimensional spatial and temporal temperature distribution in the respective measurement region 24, for the time period in which ultrasound data have been acquired for the respective measurement region 24, as described, for instance, in the above mentioned article by A. Anand et al., which is herewith incorporated by reference.

In this embodiment the temperature distribution measuring unit 13, 71 and the temperature measurement control unit 22 are adapted such that in a reference data acquisition stage the ultrasound probe 71 acquires the reference ultrasound data for the different measurement regions 24 at a known reference temperature being, in this embodiment, 37 degrees Celsius and that in a temperature distribution measurement stage the ultrasound probe 71 acquires actual ultrasound data and the ultrasound thermometry unit 13 determines the temperature distributions in the different measurement regions 24 depending on respective actual ultrasound data acquired for the respective measurement region 24, the reference ultrasound data acquired for the respective measurement region 24 and the known reference temperature.

The system 1 further comprises a model providing unit 14 for providing a model of the object describing a model temperature distribution in the measurement regions 24 for time periods, in which the respective temperature distribution has been measured in the respective measurement region, and for time periods, in which the respective temperature distribution has not been measured in the respective measurement region 24, depending on modifiable model parameters. The modifiable parameters include thermal parameters like the thermal conductivity and electrical parameters like the electrical conductivity of the liver 20.

The system 1 also comprises a temperature distribution estimating unit 15 for determining estimated spatially and temporally dependent temperature distributions in the different measurement regions for time periods, in which the respective temperature distribution has not been measured in the respective measurement region 24, by modifying the model parameters such that a deviation of the model temperature distribution in the different measurement regions 24 for the time periods, in which the respective temperature distribution has been measured in the respective measurement region 24, from the measured temperature distributions in the different measurement regions 24 is minimized and by determining the estimated temperature distributions from the modified model.

In an embodiment the model providing unit 14 is adapted to provide the model of the object describing the model temperature distribution such that the model temperature distribution does not only cover the measurement regions 24, but also a region within the person 3 directly adjacent to the tip 5 of the ablation needle 2, wherein the temperature distribution estimation unit 15 can be adapted to determine estimated temperature distributions in the different measurement regions 24 for time periods, in which the respective temperature distribution has not been measured in the respective measurement region 24, by modifying the model parameters such that a deviation of the model temperature distribution in the different measurement regions 24 for the time periods, in which the respective temperature distribution has been measured in the respective measurement region 24, and of the model temperature distribution in the region directly adjacent to the tip 5 of the ablation needle 2 from the measured temperature distributions in the different measurement regions and from the temperature measured by the temperature sensing elements at the tip 5 of the ablation needle 2 is minimized.

The model providing unit 14 may be further adapted to provide the model such that the model temperature distribution also covers a non-measurement region 24 of the person 3, in which a temperature distribution is not measured, wherein in this case the temperature distribution estimation unit 15 can be adapted to determine an estimated temperature distribution in the non-measurement region by modifying the model parameters such that a deviation of the model temperature distribution in the different measurement regions 24 for the time periods, in which the respective temperature distribution has been measured in the respective measurement region 24, from the measured temperature distribution in the different measurement regions 24 is minimized and by determining the estimated temperature distribution in the non-measurement region from the modified model. Also in this case the model can consider the temperature at the region directly adjacent to the tip 5 of the ablation needle 2, in order to consider also the temperature of this region measured by the temperature sensing elements at the tip 5 of the ablation needle 2 during the minimization process.

The temperature distributions are estimated, in particular, the minimization process is performed, while the person 3, in particular, the tumor within the liver 20 of the person 3, is heated. This allows monitoring the ablation procedure by determining the temperature distribution within the person 3, in particular, within the liver 20 of the person 3, also if the temperature is larger than, for instance, 50 degrees Celsius in certain regions within the person 3.

At the beginning of the minimization process the provided model can be initialized by using initial model parameters, which are person-specific. For example, the ultrasound probe 71 and ultrasound thermometry unit 13 can be adapted to measure the velocity of blood flowing through a vessel within the person based on a Doppler ultrasound technique, wherein this measurement can be performed before the person 3 is heated by applying the ablation energy. However, the estimated temperature distribution can also be determined, without performing this prior ultrasound measurement, wherein in this case, for instance, already known model parameters like model parameters known from literature can be used as initial model parameters, which are then modified during the minimization process.

The temperature distribution measurement unit 13, 71, the model providing unit 14 and the temperature distribution estimating unit 15 form a temperature distribution determining apparatus 21 for determining an overall temperature distribution within the person 3 covering the different measurement regions 24 also for times at which a temperature distribution has not been measured in the respective measurement region and optionally covering further regions within the person 3 like the region directly adjacent to the tip 5 of the ablation needle 2 and one or several non-measurement regions within the person 3, in which a temperature distribution has not been measured. Preferentially, the temperature distribution determining apparatus 21 is adapted to determine an overall temperature distribution covering at least the tumor to be ablated and a wide safety margin around the tumor, which includes, for instance, adjacent tissue, neighboring organs, et cetera.

The temperature distribution determining apparatus 21 further comprises an ablated region determining unit 16 for determining an ablated region defining a region within the object that has been ablated, wherein the ablated region determining unit 16 is adapted to determine the ablated region by determining a part of the person 3 in which the overall temperature distribution comprises a temperature being larger than a predefined temperature threshold. The temperature distribution determining apparatus 21 also comprises a region of interest providing unit 17 for providing the region of interest being, in this embodiment, a tumor region, which should be ablated, wherein the determined ablated region and the tumor region can be shown on a display 19. For instance, an overlay of the determined ablated region and the tumor region can be shown on the display 19. The predefined temperature threshold is, for instance, 60, 65 or 70 degrees Celsius.

The ablation energy control unit 12 can be adapted to control the ablation needle 2, i.e. the power of the ablation, depending on the determined overall temperature distribution. In particular, the ablation energy control unit 12 can be adapted to control the ablation power such that the tumor region is completely ablated.

Referring again to FIG. 1, the system 1 comprises a position detection system 6 for detecting the position of the tip 5 of the ablation needle 2 within the person 3. In this embodiment the position detection system 6 is an x-ray fluoroscopy system, in particular, an x-ray C-arm system. The x-ray fluoroscopy system comprises an x-ray source 7 for generating x-rays 8 which traverse the person 3 on the table 4, wherein the x-rays 8, which have traversed the person 3, are detected by an x-ray detector 9. The x-ray fluoroscopy system 6 further comprises a fluoroscopy control unit 10 for controlling the x-ray source 7 and the x-ray detector 9. The x-ray detector 9 generates x-ray images of the person 3, which can be shown on the display 19. On the generated x-ray images the tip 5 of the ablation needle 2 is visible within the person 3 such that the x-ray images show the position of the tip 5 of the ablation needle 2 within the person 3. In other embodiments other position detection systems for detecting the position of the needle tip within the person can be used like position detection systems which are based on electromagnetic sensors, ultrasound sensors, et cetera.

In this embodiment the ablation needle 2 is navigated directly by hand. In another embodiment the system can further comprise a navigation unit for navigating the ablation needle, in particular the needle tip, to a desired location within the person. The navigation unit can be adapted to allow a user to navigate the ablation needle completely by hand or semi-automatically. The ablation needle may comprise built-in guiding means, which can be controlled by the navigation unit. The ablation needle can, for example, be steered and navigated by the use of steering wires, in order to guide the needle tip to a desired location within the person.

Thermal ablation techniques are excellent alternatives to major surgery, which can pose a risk even with the most experienced surgeon. These techniques are minimally invasive requiring only needles, which may be adapted to perform an RF therapy, a cryotherapy or a microwave ablation therapy, or they are non-invasive, wherein, for instance, a non-invasive heat source such as an ultrasound heating source like a high intensity focused ultrasound (HIFU) source is used. In most of the procedures, cancerous tissue is heated to temperatures above 60 degrees Celsius and coagulated.

For performing an RF ablation (RFA) procedure the system described above with reference to FIG. 1 comprises a probe with an active electrode tip, i.e. the ablation needle, through which preferentially a 460 to 500 kHz alternating current is conducted. The current propagates through the body of the person 3 to grounding pads (not shown in FIG. 1 for clarity reasons) placed either on the back or the thigh of the person 3. The current causes ionic agitation and frictional heating. Heat is then dissipated through thermal conduction to ablate the tumor region. In this embodiment RFA is used to treat liver cancer.

In the embodiment described above with reference to FIG. 1 RFA is performed under x-ray guidance by using an x-ray C-arm system. However, the RFA can also be performed by using another guidance system, which may be based on ultrasound imaging, computed tomography (CT) imaging or magnetic resonance imaging (MRI) guidance. A follow-up examination is preferentially done by using a CT scan or MRI scan within, for example, a month to assess effectiveness of ablation and again at three month intervals along with tumor markers to detect residual disease or recurrence. After state of the art ablation procedures have been performed, relatively high recurrence rates are often observed because of the often present inability to monitor and control ablation size sufficiently to adequately kill the tumor cells. The system described above with reference to FIG. 1 provides therefore realtime feedback to the clinician by providing a temperature map of the ablated zone. This could also be achieved with reasonable accuracy with MR based temperature imaging. However, MRI is expensive and may not be readily available. Ultrasound is another modality that may be used for image guidance during placement of the needle. Due to its ease of use and availability it may be a preferred method for monitoring the lesions. However, in the prior art ultrasound is used generally for monitoring the treatment by visualizing the hyperechoic lesions on a B-mode image. Such visualization is only approximate and not a good indicator of the treatment efficacy.

The underlying principle of ultrasound thermometry is that the speed of sound in tissue changes as a function of temperature which manifests as apparent shifts, i.e. displacements, in ultrasound echoes. The resulting "temperature-induced strain", which is mathematically derived by differentiating the displacement along the ultrasound beam direction, is nominally proportional to the temperature rise in the range up to 50 degrees Celsius. However, the problem lies in the variation in trend of the temperature dependence of speed of sound for various tissues. For example, for liver tissues the speed of sound increases approximately linearly with temperature up to a temperature range of 50 degrees Celsius, after which the trend plateaus. Hence, there is no sensitivity to ultrasound echo shifts with temperatures beyond this temperature range. Also, with the onset of tissue necrosis and the resulting changes in tissue structure, the signature of the ultrasound echoes changes significantly and makes the comparison of ultrasound echoes to determine the displacement difficult. Therefore, for temperatures above 50 degrees Celsius the ultrasound thermometry, which is based on tracking changes in speed of sound, is not a reliable indicator of temperature in the tissue. Thus, in the embodiment described above with reference to FIG. 1 ultrasound data are acquired in a measurement region, until the temperature distribution measured in this measurement region includes a temperature exceeding 50 degrees Celsius, wherein then ultrasound data are acquired in another measurement region being more distant to the ablation needle 2 and having therefore only temperatures being smaller than 50 degrees Celsius.

The temperature distribution determining apparatus 21 is adapted to i) measure ultrasound echo shifts in measurement regions 24 and in time periods, in which the temperature is less than 50 degrees Celsius, ii) couple these echo shifts to the model, i.e. to the thermal model, provided by the model providing unit 14 and iii) use the thermal model to infer temperatures over a larger volume including the core of the heating zone and for time periods, in which the temperature distribution has not been measured in the respective measurement region. The temperature distribution determining apparatus 21 is designed so that it is not necessary to perform a test shot, i.e. it is not necessary to perform the ultrasound thermometry procedure before applying the ablation energy. The relevant parameters needed by the model are estimated during the ablative treatment itself. The goal of this approach is to provide the physician with an estimated temperature map, which also covers the ablation zone.

The temperature distribution determining apparatus 21 is preferentially adapted to use ultrasound thermometry to continuously monitor the temperature within the person 3 during the ablation procedure, wherein the temperature is monitored in the measurement regions, in which the temperature is below 50 degrees Celsius and consequently estimates the temperature in other regions, in which the temperature is higher than 50 degree Celsius, with a thermal model based approach. By using this approach the temperature distribution determining apparatus 21 may solve following problems of the prior art.

The extent of an ablated region may be determined more accurately. Moreover, in the prior art ultrasound B-mode inspection guided by hyperechoic visualization of the ablated region is often not accurate, which may render it difficult to assess the effectiveness of therapy. The hyperechoes visualized on B-mode images are caused by gas and vapor bubbles. In order to generate these bubbles and visualize the treatment region on ultrasound, an ablation treatment protocol involves heating to temperatures in the order of 100 degrees Celsius which is overkill for achieving necrosis that only requires temperatures up to 70 to 80 degrees Celsius. Hence, if ultrasound B-mode imaging is used for visually monitoring the ablation procedure, the treatment time is longer than it needs to be. Furthermore, known ultrasound thermometry techniques cannot be used in monitoring the ablated region, when it has a temperature exceeding about 50 degrees Celsius. In addition, bubbles released in the treatment region may it make difficult to reliably use ultrasound.

The temperature distribution determining apparatus 21 is adapted to utilize ultrasound thermometry for measuring temperatures in one or several measurement regions, in which the temperature is actually below 50 degrees Celsius. If in a measurement region the measured temperature exceeds 50 degrees Celsius, the measurement of the temperatures is continued in another measurement region being more distant to the ablation needle 2 and having temperatures below 50 degrees Celsius. Subsequently, the evolution of the three-dimensional measured temperature distributions is used in conjunction with the thermal model based approach to predict temperature rises in other regions, in particular, in regions being closer to the ablation needle 2, for time periods in which temperatures have not been measured in these regions. In this treatment regimen the robustness of thermal strain derived temperature data obtained at in low-temperature region is utilized for the accurate prediction of temperatures in a high-temperature region, in particular, in the tumor margin where the ablative therapy is to be performed. By following the above procedure, ultrasound data is obtained away from the bubbles released during the procedure, wherein the ultrasound data are acquired for regions with a low to moderate increase in temperatures, i.e. for regions within a temperature range of about 37 to 50 degrees Celsius. In addition, the thermal model preferentially takes into account the local temperature dependence on tissue properties and blood vessel perfusion to provide an accurate temperature map in the ablated region.

Preferentially in a pretreatment phase the model providing unit 14 provides the thermal model describing an initial model temperature distribution. For providing this model the model providing unit 14 uses medical images of the liver 20 including the tumor region like CT images or MR images. The tumor and other structures like blood vessels are identified and segmented in the medical images and this information is used together with initial model parameter values for providing an initialized thermal model. For instance, thermal and electrical parameters of the different identified and segmented structures can be initially provided for providing an initial thermal model. The initial model parameters can be tissue properties like the thermal conductivity and the electrical conductivity of different kinds of tissue or other parameters like perfusion parameters, directional flow parameters, parameters of the tip of the ablation needle, et cetera. Perfusion parameters and directional flow parameters may be initially determined by using already known information, which may be known from other measurements, which have been performed before. For instance, an ultrasound Doppler measurement can be performed, in order to determine typical flow velocities and, thus, directional flow parameters and perfusion parameters. In an embodiment the initial model has already been determined and initialized in advance and just needs to be loaded from the model providing unit 14.

The thermal model is preferentially a finite element implementation of the bioheat transfer equation (BHTE) proposed by H. H. Pennes, for example, in the article "Analysis of tissue and arterial blood temperatures in the resting human forearm", 85:5-34, Journal of Applied Physiology (1998), which is herewith incorporated by reference.

The bioheat transfer equation models thermal diffusion and perfusion in tissue. It includes a modeling of the RFA heat source, wherein a Laplace equation is implemented. The model considers directional flow in large blood vessels by using equations for heat transfer in fluids. In the case of a model for liver tissue initial model parameters are, for instance, an electrical conductivity of 0.148 S/m, a thermal conductivity of 0.465 W/mC, a density of 1060 kg/m$^3$, a heat capacity of 3600 J/Ckg and a perfusion rate of $6.4 \times 10^{-3}$/s. Further initial model parameters can be properties of the ablation needle as documented by the respective manufacturer, in order to consider an influence of the ablation needle properties on the electrical current distribution and the heat transfer.

During the treatment phase the ultrasound thermometry is performed in the different measurement regions 24 in the different time periods, in which the temperature distribution measured in the respective measurement region 24 is below 50 degrees Celsius, wherein the ultrasound probe 71 performs, for instance, a three-dimensional ultrasound backscatter acquisition procedure, wherein optionally a respiratory gating can be performed. The ultrasound thermometry unit 13 estimates then ultrasound echo shifts from the acquired three-dimensional ultrasound backscatter data, whereupon the thermal strain and finally the temperature is estimated by the ultrasound thermometry unit 13.

In this embodiment the ultrasound thermometry is performed such that during the treatment phase the temperature distributions are measured consecutively in the different measurement regions 24, wherein a) in a first time period the temperature distribution is measured in a first measurement region being closest to the ablation needle 2 until the temperature in the first measurement region exceeds 50 degrees Celsius, b) in a second time period, which starts when the temperature in the first measurement region exceeds 50 degrees Celsius, the temperature distribution is measured in a second measurement region being more distant to the ablation needle 2 than the first measurement region until the temperature in the second measurement region exceeds 50 degrees Celsius, c) in a third time period that starts when the temperature in the second measurement region exceeds 50 degrees Celsius the temperature distribution is measured in a third measurement region being more distant to the ablation needle 2 than the second measurement region until the temperature in the second measurement region exceeds 50 degrees Celsius, and so on. Thus, during the treatment the ultrasound echoes are analyzed for apparent displacements as a result of the heating in the respective measurement region, wherein these displacements, which can also be regarded as shifts, are converted to thermal strain values and finally to the temperature and wherein for determining the temperature in the respective measurement region depending on the thermal strain values known assignments between thermal strain values and temperatures can be used, which can be predetermined by calibration measurements.

During the ultrasound thermometry procedure, i.e. in parallel, the thermal model is executed with the initialized parameters, thereby generating an actual spatial temperature estimation, which is compared with the already measured temperature distributions obtained from the ultrasound thermometry procedure. Using this comparison, the model parameters are constantly updated using established minimization methods to minimize the difference between the model prediction and the ultrasound experimental data. The model parameters, which are optimized in this way, include, for instance, thermal constants such as the thermal diffusivity, electrical properties such as the electrical conductivity, properties of heat sinks caused by perfusion, convective cooling due to blood flow, et cetera. This optimization process provides flexibility in the model, which allows accounting for local heterogeneities that are to be expected in biological tissue. The model parameters of the thermal model can be continuously updated based on the already measured temperature distributions and optionally also based on an actually estimated temperature distributions obtained from running the thermal model.

For executing the model known multi-physics simulation tools like COMSOL can be used, which combine electrical heat generation and the subsequent heat transfer in the medium. Heat sinks are large blood vessels in the vicinity of the ablation zone. They can be characterized by the flow rate, the flow direction and the location and size of these vessels with respect to the energy application element. These properties can be incorporated in the bioheat transfer equation, and these properties and further properties of the model can be optimized such that a deviation between the model temperature distribution and the measured temperature distributions is minimized.

As the model parameters are optimized, a temperature map is generated and updated in a region of interest being preferentially a treatment region of interest covering the tumor. The temperature map can be used to generate an ablation contour by defining the region within the liver 20, which is or has been heated to a temperature being larger than a predefined temperature threshold. During the entire process in the treatment phase the ultrasound echo shifts are constantly analyzed such that there is a realistic feedback to the model that takes into account, for instance, the tissue properties and the perfusion effects on the spatial-temporal distribution of the heat.

For updating the model parameters in the treatment phase not only the measured temperature distribution in the measurement regions 24 may be compared with the estimated temperature distribution obtained from the thermal model, but additionally also the temperature at the tip of the ablation needle as measured by, for instance, thermocouples may be compared with the estimated temperature distribution obtained from the thermal model, wherein the model parameters can be optimized such that the estimated temperature distribution fits as good as possible to the measured temperature distributions in the measurement regions measured by ultrasound thermometry and the temperature measured by the thermocouples at the tip of the ablation needle.

The temperature map can be used as a feedback to control a power output of the ablation energy control unit 12 controlling the application of the RF ablation energy.

In a post-treatment phase the temperature map and/or the ablation contour may be shown overlaid on the region of interest, in particular, overlaid on the tumor region, to get a realistic sense of the effectiveness of the treatment. It may then be decided based on this overlay image, whether an additional treatment is necessary.

Figure 4:
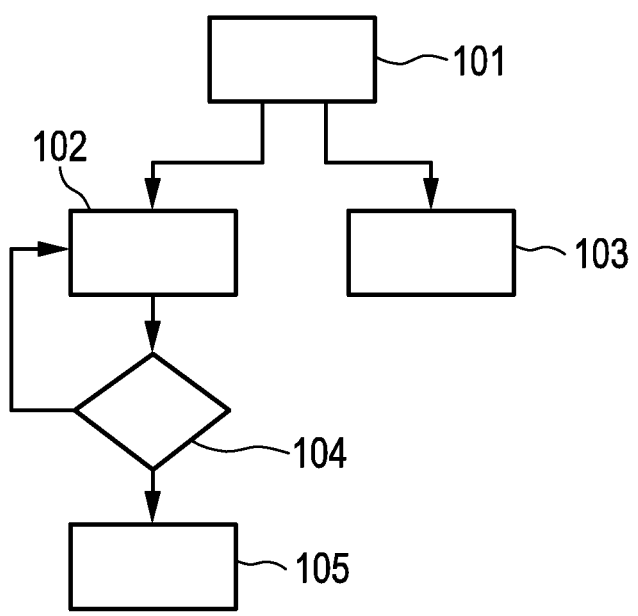
FIG. 4 shows a flowchart exemplarily illustrating an embodiment of a temperature distribution measuring method for measuring a temperature distribution within the object caused by heating the object.

In the following an embodiment of a temperature distribution measuring method will exemplarily be described with reference to a flowchart shown in FIG. 4.

In step 101 the tip 5 of the ablation needle 2 is navigated into the liver 20 such that the tip is located within a tumor region within the liver 20. Moreover, in step 101 an initial thermal model is provided by the model providing unit 14. Step 101 is performed in the pre-treatment phase.

Then, in step 103 the treatment starts by applying ablation energy to the tumor region, i.e. by heating the tumor region, and in step 102 the temperature distribution is measured in a first measurement region 24 within the liver 20 by the temperature distribution measuring unit 13, 71.

In step 104 it is checked whether the temperature distribution measured in the first measurement region includes a temperature above 50 degrees Celsius, wherein, if this is the case, the temperature measurement control unit 22 controls the temperature distribution measuring unit 13, 71 such that the temperature measurement continues in step 102 with a second measurement region having a larger distance to the tip 5 of the ablation needle 2. If the temperature distribution measured in the first measurement region does not include a temperature being larger than 50 degrees Celsius, the temperature measurement continues in step 102 with still measuring the temperature distribution in the first measurement region. Moreover, the measured temperatures, which do not include a temperature being larger than 50 degrees Celsius, are provided to the temperature distribution estimation unit 15, wherein in step 105 the temperature distribution estimation unit 15 determines an overall temperature distribution, in particular, determines estimated temperature distributions in the different measurement regions 24 for time periods, in which a temperature distribution has not been measured in the respective measurement region, and also in other regions within the liver 20, in which a temperature distribution has not been measured, by modifying the model parameters of the thermal model such that a deviation of the model temperature distribution in the different measurement regions for the time periods, in which the respective temperature distribution has been measured in the respective measurement region, from the already measured temperature distributions in the different measurement regions is minimized and by determining the estimated temperature distributions from the modified model.

Steps 102 and 104 are performed in a loop, wherein this loop and step 105 are performed in parallel, i.e. the measured temperature distributions are continuously fed to the temperature distribution estimation unit 15, in order to continuously generate an updated overall temperature distribution. The temperature distributions determination steps 102, 104 and 105 on the one side and the ablation step 103 on the other side are also performed in parallel such that during the ablation procedure a user like a physician can monitor the development of the temperature distribution and stop the ablation procedure, if the user is satisfied with the generated temperature distribution. Thus, steps 102 to 105 may be performed until the user stops the procedure or until an abort criterion has been fulfilled. The measurement regions 24 have different distances to the tip 5 of the ablation needle 2, i.e. the location, at which the ultrasound measurement is performed, is not stationary. If this location would be stationary, this could result in sub-optimal, for instance, higher or lower, temperatures being measured and the locations could have a high thermal gradient. This would affect the accuracy of the model parameters derived from these measurements in-situ at the ablation site and the estimated therapy end point, which may be reached when a certain thermal dose has been reached, which may be calculated based on the measured temperature distribution.

The temperature distribution measuring apparatus described above with reference to FIG. 1 provides an adaptive ultrasound thermometry measurement scheme, where the measurement location is changed during the therapy, especially to ensure that an optimal temperature rise, i.e. in this embodiment a temperature rise from 37 to 50 degrees Celsius, is used.

Although in the embodiment described above with reference to FIG. 1 the heating source is an ablation electrode, which may be a single tine ablation electrode, at a tip 5 of an RF ablation needle 2, in other embodiments also other heating sources can be used like a HIFU source or a microwave source, in particular, to perform an ablation procedure.

The temperature distribution measuring apparatus 21 is adapted to track the local temperature rise using ultrasound at a couple of planes 24 parallel to the RF ablation tine, i.e. parallel to the heating source. In contrast to the stationary situation in which the temperature is tracked in the same plane at all times, in the dynamic situation as the heating progresses different spatial locations are used to compute the temperature rise.

The temperature distribution measuring apparatus 21 preferentially addresses the following problems. When the scan plane would remain stationary, it could not be located close to the ablation tine, i.e. the heating source, because the temperature would increase to beyond 50 degrees Celsius and the measurements would not be useful. If the scan plane would be placed far enough to ensure that the temperature rise is never larger than 50 degrees Celsius, the temperature rise would be extremely low at the initial time points and hence the accuracy of the temperature measurement would be relatively low. Furthermore, in addition to providing the measured temperature rise using ultrasound to the thermal model, one of the critical inputs is the spatial position where the respective measurement was made with respect to the heating source. When the thermal gradients are high, the uncertainty in the position of the scan plane can result in large errors in the model parameters. It is therefore preferred that the position of the measurement region, in particular, the scan plane position, is dynamically moved such that the measurement region is mostly or always in a spatial region with relatively low thermal gradients.

Figure 5:
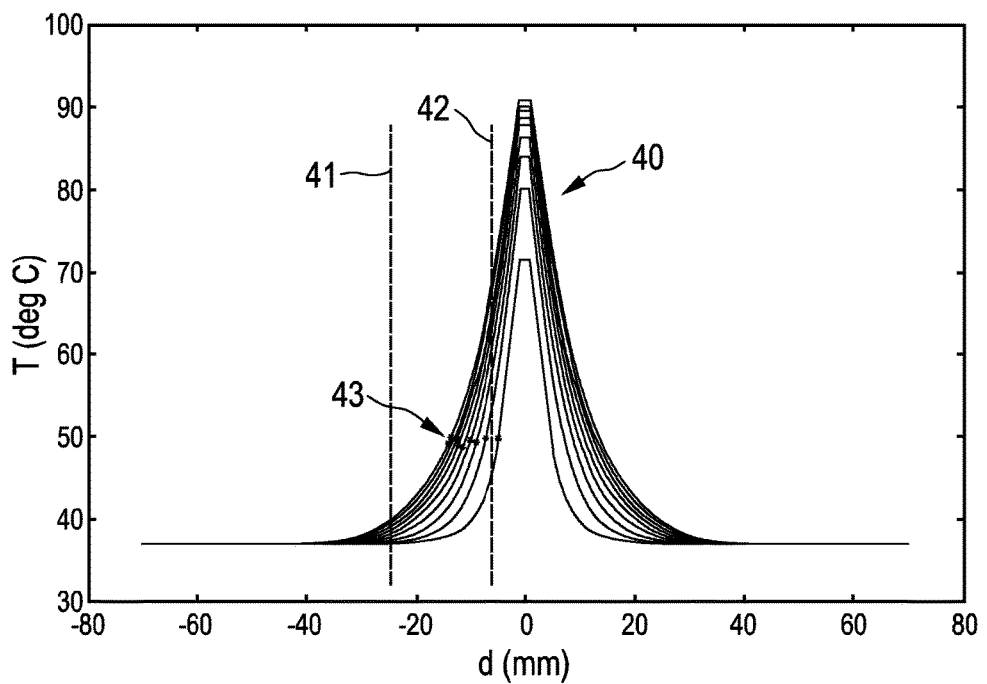
FIG. 5 shows exemplarily a temperature profile.
Figure 6:
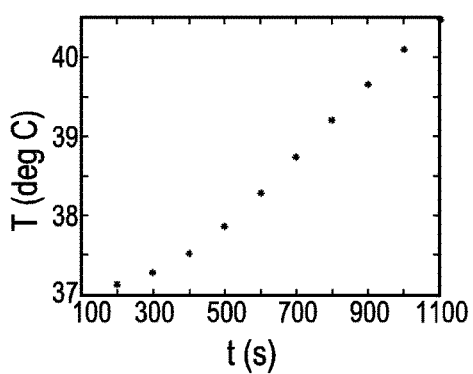
FIG. 6 shows exemplarily an increase of a temperature with time at a distance of 25 mm from the ablation needle.
Figure 7:
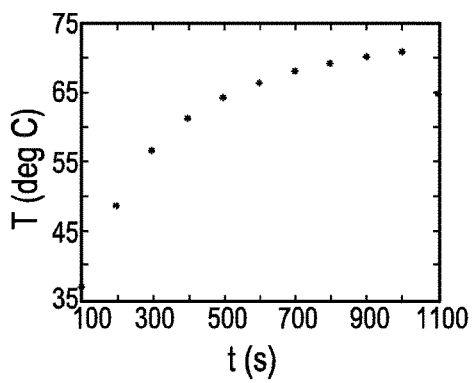
FIG. 7 shows schematically an increase of a temperature with time at a distance of 5 mm from the ablation needle.

FIG. 5 exemplarily illustrates a typical temperature profile along a line perpendicular to the ablation tine, i.e. to the heating source, intersecting it at the midpoint of the exposed electrode of the ablation tine. The ablation tine is at the distance d=0 along the horizontal axis. The line plots 40 show the evolution of the temperature T every 100 s during an RF ablation heating procedure in liver tissue. As can be seen in FIG. 5, the peak tine temperature is larger than 90 degrees Celsius. FIG. 6 exemplarily illustrates the temperature evolution at a distance of 25 mm from the position of the heating source, i.e. FIG. 6 exemplarily illustrates the temperatures along the line 41 in FIG. 5. FIG. 7 exemplarily illustrates the temperature evolution at a distance of 5 mm from the position of the heating source, i.e. FIG. 7 shows the temperatures along the line 42 in FIG. 5. These distances, i.e. 5 mm and 25 mm, represent locations where an ultrasound scan plane, i.e. a measurement region, could be placed in a stationary measurement scheme. However, both locations have disadvantages. At the distance of 25 mm the temperature rise is barely 3.5 degrees Celsius at the end of the therapy as shown in FIG. 6. Thus, at this distance the applicable range of temperatures is not well utilized. At the distance of 5 mm the temperature rises up to a temperature close to 70 degrees Celsius as shown in FIG. 7. This would render ultrasound-based temperature measurement techniques difficult to implement for the above mentioned reasons. These problems illustrated in FIGS. 6 and 7 are preferentially solved by the temperature distribution measuring apparatus 21.

Figure 8:
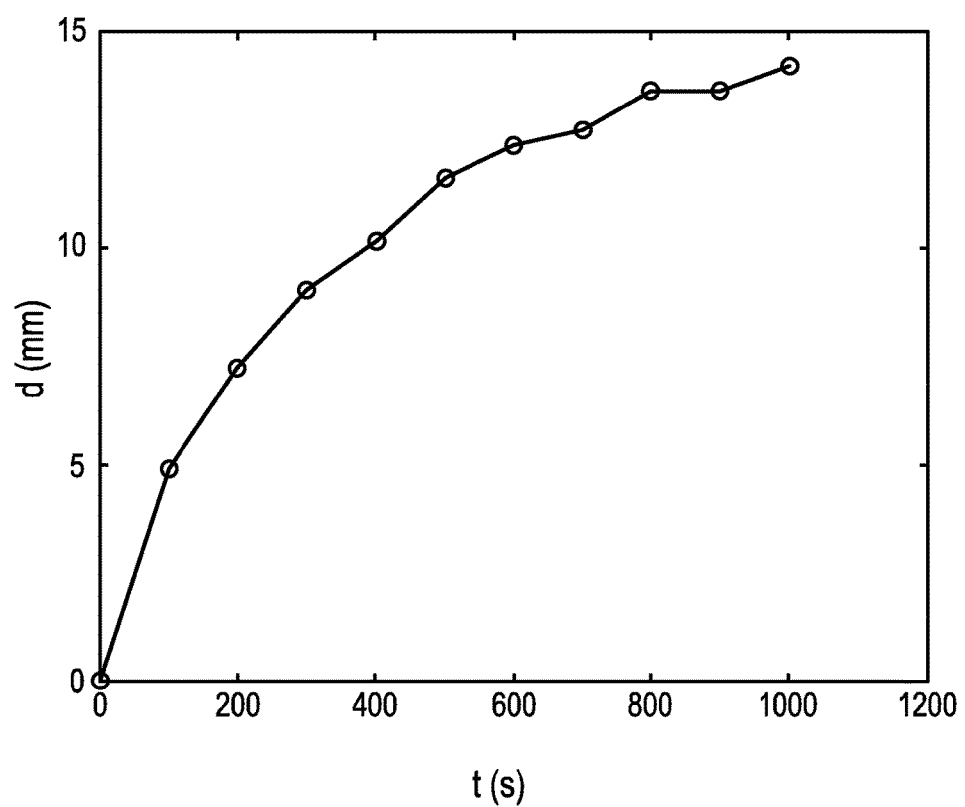
FIG. 8 shows exemplarily positions of measurement regions depending on time.

The temperature distribution measuring apparatus 21 provides the flexibility to change the position of the measurement region, i.e. of the ultrasound scan plane, dynamically, which in turn allows to make the ultrasound temperature measurements in the most favorable locations, wherein then these ultrasound temperature measurements can be fed to the thermal model. The optimum positions, i.e. the optimal distances at which the measurement regions should be placed, can be determined from FIG. 5 where the blue asterisks 43 represent the locations at which the temperature is close to 50 degrees Celsius at different time instants. These blue asterisks 43 versus time, i.e. the corresponding distances d versus t, are shown in FIG. 8. FIG. 8 exemplarily illustrates a plot representing distances to the heating source, at which the measurement regions, i.e. in this embodiment the ultrasound scan planes, are preferably placed, in order to have the optimal temperature change that can be measured with the ultrasound technique.

The temperature distribution measuring apparatus has the ability to change the position of the scan plane, i.e. of the measurement region, where the ultrasound thermometry measurement is obtained. The temperature distribution measuring apparatus preferentially comprises an ultrasound probe, which may include a one-dimensional transducer or a two-dimensional transducer. If the ultrasound probe includes a one-dimensional transducer, the ultrasound probe is preferentially adapted such that the one-dimensional ultrasound transducer can be mechanically translated to obtain the temperature measurements at the different spatial locations. If the ultrasound probe includes a two-dimensional ultrasound transducer, it has preferentially scan planes positioned at the different locations, at which the ultrasound temperature measurements should be performed. The temperature distribution measuring apparatus, in particular, the temperature measurement control unit of the temperature distribution measuring apparatus, which may comprise a corresponding processing unit, preferentially evaluates the temperature measurements at each scan plane location, i.e. in each measurement region, in order to determine if the temperature rise is within a predefined allowable range, for instance, between 37 degrees Celsius and 50 degrees Celsius. When the temperature rise exceeds beyond this range, the temperature data from that scan plane are rejected and the next distant location is utilized for analysis.

Although in above described embodiments a measurement region, in which temperatures are actually measured, is formed by a single plane only, i.e. although in above described embodiments the different measurement regions are formed by a single movable ultrasound scan plane only, in other embodiments a measurement region, at which the temperature is actually measured, can be formed by several planes, in particular, by several ultrasound scan planes, such that at the same time the temperature can be measured in different planes. If in at least one of these planes the temperature rises above an upper temperature limit like 50 degrees Celsius, the measurement region may be modified by excluding this plane from further temperature measurements or by moving this plane to another more distant position. The planes may be vertical or horizontal planes, wherein, if the scan plane is horizontal, it may be scanned in a C-scan manner. Moreover, instead of being planar the measurement regions can also have another shape, i.e. they can be non-planar, in particular, curved. Moreover, although in above described embodiments the scan planes, i.e. the planar measurement regions, are parallel to the direction of the ablation tine, in other embodiments they may also be perpendicular to the ablation tine.

If in an embodiment the ultrasound probe comprises a one-dimensional ultrasound transducer, the transducer is preferentially translated mechanically at the start of the treatment to obtain reference ultrasound data at different measurement positions in a reference data acquisition stage, i.e. reference ultrasound data are acquired in the different measurement regions. Preferentially, the reference sweep in the reference data acquisition stage provides baseline information at a temperature of 37 degrees Celsius. Essentially, this can be regarded as a snapshot of the signature of RF echoes at t=0 before the start of the treatment. The reference ultrasound data can be used during the treatment phase, i.e. during the temperature distribution measurement stage, for determining actual temperature distributions in the different measurement regions by ultrasound thermometry based on differences between the ultrasound backscatter acquired during the reference data acquisition stage and the actual ultrasound backscatter acquired during the treatment phase.

The distance between the scan positions, i.e. the positions of the planar measurement regions, are preferentially determined based on a planned target volume of a lesion to be created and the number of required scan planes. Also a priori information from a thermal model, which may be the model provided by the model providing unit 14 and which indicates the thermal gradient at the different positions, is preferentially used to determine the positions of the planar measurement regions.

After the reference scan has been performed in the reference data acquisition stage, the one-dimensional transducer is repositioned at a first position typically closest to the ablation tine. After the therapy has been started, the temperature rise in the first plane is measured by using a comparison with the corresponding reference frame. The temperature rise measured in this first plane, i.e. in the first measurement region, is continuously fed to the provided thermal model. When the measured temperature in the first plane is close to 50 degrees Celsius, the temperature measurement at this location is stopped and the one-dimensional transducer is moved to the next spatial location, i.e. to the second position, away from the ablation tine. Temperature measurements from the first position will be appended to the subsequent measurements from a second position, from a third position and so forth, and optimal model parameters will be estimated based on these temperature measurements as constraints. Based on the optimal model parameters, i.e. based on the corresponding optimized thermal model, the three-dimensional temperature distribution over the entire volume can be determined.

Although in above described embodiments reference ultrasound data have been acquired in a reference data acquisition stage by performing a reference sweep before the start of the ablation treatment, in other embodiments the temperature distribution measuring method may be performed without such a reference ultrasound data acquisition. In this case the thermal model provided by the model providing unit 14 can be used to determine reference temperatures for measured ultrasound data. In particular, the provided thermal model of the object may describe a model temperature distribution in the measurement regions, in which the respective temperature distribution has been measured already during the therapy, and in the measurement regions, in which the respective temperature distribution has not been measured already during the therapy, depending on the modifiable model parameters, wherein the temperature distribution estimation unit may be adapted to determine the reference temperature for a respective measurement region, in which the respective temperature distribution has not been measured already, by modifying the model parameters such that a deviation of the model temperature distribution in the measurement regions, in which the respective temperature distribution has been measured already, from the measured temperature distributions in the measurement regions, in which the respective temperature distribution has been measured already, is minimized and by determining the reference temperature from the modified model. For instance, the one-dimensional ultrasound transducer may be initially placed at the first position from a time $t_0$ up to a time $t_1$, wherein at this first position, i.e. in the corresponding first measurement region, the temperature is measured over time up to the temperature at the time $t_1$. The time $t_1$ may be defined by the time at which the measured temperature is close to, i.e. almost, equal to or just slightly larger than 50 degrees Celsius. Then, the one-dimensional ultrasound transducer is moved to the second position at the time $t_1$, wherein the temperature at the second position, i.e. in the second measurement region being more distant to the ablation time, at the time $t_1$, i.e. or, to be more specific, at a time $t_1+\Delta t$, wherein $\Delta t$ is the time for moving from the first position to the second position, is predicted from the thermal model based on the already performed temperature measurements in the first measurement region. This predicted temperature at the time $t_1$ in the second measurement region is the reference temperature for the measurement in the second measurement region and the reference ultrasound data are the ultrasound data acquired at the time $t_1$ in the second measurement region. After the one-dimensional transducer has been moved to the second position, the temperature rise measured at this location from the time $t_1$ to the time $t_2$ is added to the starting temperature derived from the thermal model at the time $t_1$ to obtain the absolute temperature at the time $t_2$. The same procedure can be performed for the further measurement regions, for instance, for third, fourth and fifth measurement regions and corresponding time intervals $t_2$ to $t_3$, $t_3$ to $t_4$ and $t_4$ to $t_5$, respectively. As data are available at different spatial positions away from the ablation time, very robust data are provided for estimating thermal parameters that determine the spatial-temporal heat distribution profile.

If instead of a one-dimensional ultrasound transducer a two-dimensional ultrasound transducer, i.e. a two-dimensional ultrasound array, is used, the ability to image in multiple two-dimensional scan planes is provided. The scan planes, in which the data will be acquired, i.e. the corresponding positions and thus the measurement regions, are preferentially predefined. The ultrasound data acquired in these predefined scan planes can be processed sequentially starting from scan planes closest to the ablation tine at a time $t_0$ and progressively further away at later times. The ultrasound data acquired at each of these spatial locations, i.e. in each of the planar measurement regions, can be used to determine the temperature distributions in these measurement regions by ultrasound thermometry and the determined temperature distributions can be fed to the thermal model to estimate the model parameters and the resulting overall temperature distribution. Since in this embodiment a two-dimensional ultrasound transducer is used, in a reference data acquisition stage the reference frames, i.e. the reference ultrasound data for the different measurement regions at the time $t_0$, i.e. when the temperature of the person is 37 degrees Celsius, are easily simultaneously available.

Although in above described embodiments the temperature distribution determining technique is used in connection with an RF ablation procedure, in other embodiments the temperature distribution determining technique can also be used together with other energy application procedures like other ablation procedures. For instance, the temperature distribution determining technique may also be combined with HIFU, microwave ablation, laser ablation et cetera.

Although in above described embodiments certain ultrasound thermometry techniques have been described for measuring temperature distributions in the measurement regions by ultrasound thermometry, in other embodiments also other ultrasound thermometry techniques can be used like other ultrasound thermometry techniques relying on relationships between ultrasound characteristics and temperatures of an object. Moreover, although in above described embodiments temperature distributions are determined in tissue, in other embodiments temperature distributions can be determined in other objects. For instance, temperature distributions can be determined in other parts of a living being or in a technical object.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the measuring of the temperature distribution in a measurement region, the control of the temperature distribution measuring unit such that the measurement region is modified depending on the measured temperature distribution, the provision of the model, the adaptation of the model, et cetera performed by one or several units or devices can be performed by any other number of units or devices. These procedures and/or the control of the temperature distribution determining apparatus in accordance with the temperature distribution determining method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a temperature distribution measuring apparatus for measuring a temperature distribution within an object caused by heating the object. A temperature distribution measuring unit measures the temperature distribution in a measurement region within the object, while the object is heated, and a temperature measurement control unit controls the temperature distribution measuring unit such that the measurement region is modified depending on the measured temperature distribution, in order to measure different temperature distributions in different measurement regions. This allows, for example, modifying the measurement region depending on an actually measured temperature distribution such that in the modified new measurement region the measurement of the temperature of the object can be continued, if the temperature actually measured in the current measurement region is too high for being accurately measured, thereby extending the time period in which a temperature distribution of the object can be measured.

The invention claimed is:

1. A temperature distribution measuring apparatus for measuring a temperature distribution within an object caused by heating the object, the temperature distribution measuring apparatus comprising:
   a temperature distribution measuring unit for measuring the temperature distribution in a measurement region within the object, while the object is heated, wherein the temperature distribution measuring unit comprises an ultrasound probe for acquiring ultrasound data of the measurement region and an ultrasound thermometry unit for determining the temperature distribution within the measurement region based on the acquired ultrasound data,
   a temperature measurement control unit for controlling the temperature distribution measuring unit such that the measurement region is modified depending on the measured temperature distribution, in order to measure different temperature distributions in different measurement regions,
   a model providing unit for providing a model of the object describing a model temperature distribution
   a) in the measurement regions for time periods, in which the respective temperature distribution has been measured in the respective measurement region, and
   b) in the measurement regions for time periods, in which the respective temperature distribution has not been measured in the respective measurement region, and/or in a non-measurement region within the object, in which a temperature distribution is not measured, and
   a temperature distribution estimation unit for determining estimated temperature distributions in the different measurement regions for time periods, in which the respective temperature distribution has not been measured in the respective measurement region and/or in the non-measurement region based on the measured temperature distributions by using the provided model.

2. The temperature distribution measuring apparatus as defined in claim 1, wherein the temperature measurement control unit is adapted to control the temperature distribution measuring unit such that the measurement region is modified by changing a position of the measurement region.

3. The temperature distribution measuring apparatus as defined in claim 2, wherein the object is heated by a heating source, wherein the temperature measurement control unit is adapted to control the temperature distribution measuring unit such that the measurement region is consecutively located at different positions, wherein, if the position of the measurement region is changed, it is changed from a position being closer to the heating source to a position being more distant to the heating source.

4. The temperature distribution measuring apparatus as defined in claim 1, wherein the temperature distribution measuring device is adapted to move the ultrasound probe for changing a position of the measurement region, in order to modify the measurement region.

5. The temperature distribution measuring apparatus as defined in claim 1, wherein the ultrasound probe is adapted such that a position of the measurement region is changeable without moving the ultrasound probe, in order to modify the measurement region.

6. The temperature distribution measuring apparatus as defined in claim 1, wherein the temperature measurement control unit is adapted to determine whether the measured temperature distribution in the measurement region includes a temperature outside a predefined temperature range and to control the temperature distribution measuring unit such that the measurement region is modified, if the measured temperature distribution in the measurement region includes a temperature outside the predefined temperature range.

7. The temperature distribution measuring apparatus as defined in claim 1, wherein:
   the model providing unit is adapted to provide the model of the object such that it describes the model temperature distribution depending on modifiable model parameters, and
   the temperature distribution estimation unit is adapted to determine the estimated temperature distributions in the different measurement regions for time periods, in which the respective temperature distribution has not been measured in the respective measurement region, and/or in the non-measurement region by modifying the model parameters such that a deviation of the model temperature distribution in the different measurement regions for the time periods, in which the respective temperature distribution has been measured in the respective measurement region, from the measured temperature distributions in the different measurement regions is minimized and by determining the estimated temperature distributions from the modified model.

8. A system for heating an object, the system comprising:
a heating source for heating the object, and
a temperature distribution determining apparatus for determining a temperature distribution within the object as defined in claim 1.

9. The system as defined in claim 8, wherein the system further comprises a heating source control unit for controlling the heating source depending on the determined temperature distribution.

10. The temperature distribution measuring apparatus as defined in claim 1, wherein the temperature measurement control unit is adapted to determine whether the measured temperature distribution in the measurement region includes a temperature outside a predefined temperature range and to control the temperature distribution measuring unit such that the measurement region is modified, if the measured temperature distribution in the measurement region includes a temperature outside the predefined temperature range.

11. A temperature distribution measuring method for measuring a temperature distribution within an object caused by heating the object, the temperature distribution measuring method comprising:
measuring the temperature distribution in a measurement region within the object, while the object is heated, by a temperature distribution measuring unit, wherein the temperature distribution measuring unit comprises an ultrasound probe which acquires ultrasound data of the measurement region and an ultrasound thermometry unit which determines the temperature distribution within the measurement region based on the acquired ultrasound data, and
controlling the temperature distribution measuring unit such that the measurement region is modified depending on the measured temperature distribution, in order to measure different temperature distributions in different measurement regions, by a temperature measurement control unit,
providing a model of the object describing a model temperature distribution
a) in the measurement regions for time periods, in which the respective temperature distribution has been measured in the respective measurement region, and
b) in the measurement regions for time periods, in which the respective temperature distribution has not been measured in the respective measurement region, and/or in a non-measurement region within the object, in which a temperature distribution is not measured,
by a model providing unit, and
determining estimated temperature distributions in the different measurement regions for time periods, in which the respective temperature distribution has not been measured in the respective measurement region and/or in the non-measurement region based on the measured temperature distributions by using the provided model by a temperature distribution estimation unit.

12. A computer program element comprising instructions to control a temperature distribution determining apparatus, which, when being executed by a computer, is adapted to perform the method of claim 11.

13. A non-transitory computer readable medium having stored thereon the program element of claim 12.

14. A temperature distribution measuring apparatus for measuring a temperature distribution within an object caused by heating the object, the temperature distribution measuring apparatus comprising:
a temperature distribution measuring unit for measuring the temperature distribution in a measurement region within the object, while the object is heated, wherein the temperature distribution measuring unit comprises an ultrasound probe for acquiring ultrasound data of the measurement region and an ultrasound thermometry unit for determining the temperature distribution within the measurement region based on the acquired ultrasound data,
a temperature measurement control unit for controlling the temperature distribution measuring unit such that the measurement region is modified depending on the measured temperature distribution, in order to measure different temperature distributions in different measurement regions,
a model providing unit for providing a model of the object describing a model temperature distribution
a) in the measurement regions for time periods, in which the respective temperature distribution has been measured in the respective measurement region, and
b) in the measurement regions for time periods, in which the respective temperature distribution has not been measured in the respective measurement region, and/or in a non-measurement region within the object, in which a temperature distribution is not measured, and
a temperature distribution estimation unit for determining estimated temperature distributions in the different measurement regions for time periods, in which the respective temperature distribution has not been measured in the respective measurement region and/or in the non-measurement region based on the measured temperature distributions by using the provided model, wherein the temperature distribution measuring unit and the temperature measurement control unit are adapted such that the ultrasound probe acquires reference ultrasound data for the different measurement regions at reference temperatures and actual ultrasound data for the different measurement regions and that the ultrasound thermometry unit determines a temperature distribution in a respective measurement region depending on respective actual ultrasound data acquired for the respective measurement region, the reference ultrasound data acquired for the respective measurement region and a respective reference temperature.

15. The temperature distribution measuring apparatus as defined in claim 14, wherein the temperature distribution measuring unit and the temperature measurement control unit are adapted such that in a reference data acquisition stage the ultrasound probe acquires the reference ultrasound data for the different measurement regions at known reference temperatures and that in a temperature distribution measurement stage the ultrasound probe acquires actual ultrasound data and the ultrasound thermometry unit determines the temperature distributions in the different measurement regions depending on respective actual ultrasound data acquired for the respective measurement region, the reference ultrasound data acquired for the respective measurement region and the respective reference temperature.

16. The temperature distribution measuring apparatus as defined in claim 14, wherein:
the model providing unit is adapted to provide the model such that it describes a model temperature distribution in the measurement regions, in which the respective temperature distribution has been measured already, and in the measurement regions, in which the respective temperature distribution has not been measured already, depending on modifiable model parameters, and the temperature distribution estimation unit is adapted to determine the reference temperature for a respective measurement region, in which the respective temperature distribution has not been measured already, by modifying the model parameters such that a deviation of the model temperature distribution in the measurement regions, in which the respective temperature distribution has been measured already, from the measured temperature distributions in the measurement regions, in which the respective temperature distribution has been measured already, is minimized and by determining the reference temperature from the modified model.

17. The temperature distribution measuring apparatus as defined in claim 14, wherein the temperature measurement control unit is adapted to control the temperature distribution measuring unit such that the measurement region is modified by changing a position of the measurement region.

18. The temperature distribution measuring apparatus as defined in claim 17, wherein the object is heated by a heating source, wherein the temperature measurement control unit is adapted to control the temperature distribution measuring unit such that the measurement region is consecutively located at different positions, wherein, if the position of the measurement region is changed, it is changed from a position being closer to the heating source to a position being more distant to the heating source.

19. The temperature distribution measuring apparatus as defined in claim 14, wherein the temperature distribution measuring device is adapted to move the ultrasound probe for changing a position of the measurement region, in order to modify the measurement region.

20. The temperature distribution measuring apparatus as defined in claim 14, wherein the ultrasound probe is adapted such that a position of the measurement region is changeable without moving the ultrasound probe, in order to modify the measurement region.

21. The temperature distribution measuring apparatus as defined in claim 14, wherein:
the model providing unit is adapted to provide the model of the object such that it describes the model temperature distribution depending on modifiable model parameters, and
the temperature distribution estimation unit is adapted to determine the estimated temperature distributions in the different measurement regions for time periods, in which the respective temperature distribution has not been measured in the respective measurement region, and/or in the non-measurement region by modifying the model parameters such that a deviation of the model temperature distribution in the different measurement regions for the time periods, in which the respective temperature distribution has been measured in the respective measurement region, from the measured temperature distributions in the different measurement regions is minimized and by determining the estimated temperature distributions from the modified model.

22. A system for heating an object, the system comprising:
a heating source for heating the object, and
a temperature distribution determining apparatus for determining a temperature distribution within the object as defined in claim 14.

23. The system as defined in claim 22, wherein the system further comprises a heating source control unit for controlling the heating source depending on the determined temperature distribution.

* * * * *